(12) United States Patent
Ozawa et al.

(10) Patent No.: US 7,470,548 B2
(45) Date of Patent: Dec. 30, 2008

(54) HAZARDOUS SUBSTANCE REMOVING METHOD, HAZARDOUS SUBSTANCE REMOVING MATERIAL USED THEREIN SUCH AS AIR FILTER, MASK, WIPE SHEET, AND THE LIKE, AND STORAGE METHOD THEREOF

(75) Inventors: Satoshi Ozawa, Ibaraki (JP); Jun-ichiro Arai, Ibaraki (JP)

(73) Assignee: Daikin Industries, Ltd., Osaka (JP)

( * ) Notice: Subject to any disclaimer, the term of this patent is extended or adjusted under 35 U.S.C. 154(b) by 149 days.

(21) Appl. No.: 10/544,393

(22) PCT Filed: Mar. 26, 2004

(86) PCT No.: PCT/JP2004/004375

§ 371 (c)(1), (2), (4) Date: Aug. 3, 2005

(87) PCT Pub. No.: WO2004/087224

PCT Pub. Date: Oct. 14, 2004

(65) Prior Publication Data

US 2006/0088926 A1    Apr. 27, 2006

(30) Foreign Application Priority Data

Mar. 28, 2003    (JP)    ............................ 2003-092199
Jan. 21, 2004    (JP)    ............................ 2004-013324

(51) Int. Cl.
*G01N 33/543*    (2006.01)

(52) U.S. Cl. .................................................... 436/518

(58) Field of Classification Search .................... 438/4, 438/297.1; 436/8, 518, 514, 517, 524, 528–535; 422/50; 435/287.1–287.3, 287.7
See application file for complete search history.

(56) References Cited

U.S. PATENT DOCUMENTS 4,237,234 A * 12/1980 Meunier ................. 435/287.7
4,341,755 A * 7/1982 Lindall ..................... 424/1.45
4,856,509 A     8/1989 Lemelson
5,558,869 A * 9/1996 Burks et al. ............. 424/276.1
5,651,900 A * 7/1997 Keller et al. ................ 216/56
5,731,162 A * 3/1998 Gatti et al. ................ 435/7.32
6,074,869 A * 6/2000 Pall et al. ................. 435/286.5

FOREIGN PATENT DOCUMENTS

| | | |
|---|---|---|
| EP | 0885644 A1 | 12/1998 |
| JP | 4-94717 A | 3/1992 |
| JP | 5-340948 A | 12/1993 |
| JP | 7-32860 B | 4/1995 |
| JP | 98/04334 A | 2/1998 |
| JP | 11-511237 A | 9/1999 |
| JP | 2000-279503 A | 10/2000 |
| JP | 2000-302436 A | 10/2000 |
| JP | 2001-327815 A | 11/2001 |
| JP | 2001-527166 A | 12/2001 |
| JP | 2003-33612 A | 2/2003 |
| WO | WO-98/56489 A1 | 12/1998 |
| WO | WO-99/32707 A1 | 7/1999 |

OTHER PUBLICATIONS

Microfilm of the specification and drawings annexed to the request of Japanese Utility Model Application No. 138599/1984 (Laid-open No. 54850/1986 (Toray Industries, Inc.) Apr. 12, 1986.
Derwent Abstract Accession No. 99-060070/05, Dec. 17, 1998.
Derwent Abstract Accession No. 97-035288/04, Dec. 5, 1996.
Derwent Abstract Accession No. 95-329007/43, Sep. 21, 1995.

* cited by examiner

*Primary Examiner*—Ann Y Lam
(74) *Attorney, Agent, or Firm*—Birch, Stewart, Kolasch & Birch, LLP

(57) ABSTRACT

A hazardous substance (20) is removed by using a hazardous substance removing material (10) in which a support (11) supports an antibody (12). Humidity of the ambient atmosphere of the antibody (12) is controlled so that the antibody (12) becomes active.

4 Claims, 2 Drawing Sheets

HAZARDOUS SUBSTANCE REMOVING METHOD, HAZARDOUS SUBSTANCE REMOVING MATERIAL USED THEREIN SUCH AS AIR FILTER, MASK, WIPE SHEET, AND THE LIKE, AND STORAGE METHOD THEREOF

TECHNICAL FIELD

The present invention relates to a hazardous substance removing method for air purification and the like, a hazardous substance removing material such as an air filter, a mask, a wiper sheet, and the like used therein, and a storage method thereof.

BACKGROUND ART

As methods for removing hazardous substances of microbe origin in the air such as viruses, bacteria, and the like, there are filtration using various kinds of filters, physical adhesion using adsorbents, and the like.

Japanese Patent Application Laid Open Publication No. 9-234317A discloses a virus removing filter using, as a virus-capturing body, at least one kind of sialic acid, a sialic acid derivative, and sugars, glycoproteins, and glycolipids containing the sialic acid and/or the sialic acid derivative. The publication mentions that this filter can be used in ordinary living space and efficiently removes viruses such as influenza viruses.

Japanese Patent Application Laid Open Publication No. 2001-527166A discloses a fibrous material including a plurality of interwoven threads with a high degree of microfibrillation wherein at least on thread is derivatised using cyanogen bromide to attach a natural receptor for a virus or a portion or an analogue thereof to capture a virus.

However, the methods for removing the hazardous substances in the air such as the filtration using a filter and the physical adhesion using an adsorbent are directed to capture of substances nonspecifically and have low precision. Further, in order to avoid re-floating of removed hazardous substances and to prevent multiplication of the hazardous substances so as not to allow them to serve as a new contaminant source, techniques for sterilizing and deactivating the hazardous substances must be incorporated.

Japanese Patent Application Laid Open Publication No. 8-333271A discloses an antiviral mask composed of a nonwoven fabric with which a tea extract is impregnated and ear stopper strings, wherein the nonwoven fabric with which the tea extract is impregnated is obtained in such a manner that the extract separated and refined from green tea components or black tea components is solved in purified water, is dehydrated lightly, and then, is dried. The publication mentions that this mask of the nonwoven fabric with which the tea extract is impregnate can be easily produced industrially, can maintain high virus trapping performance, can deactivate viruses, and can prevent re-entrainment of the viruses.

SUMMARY OF THE INVENTION

The present invention has its object of providing a novel hazardous substance removing method, a novel hazardous substance removing material used therein such as an air filter, a mask, a wipe sheet, and the like, and a novel storage method thereof.

To attain the above object, the present invention removes a hazardous substance (20) by using an antibody (12).

Specifically, in a hazardous substance removing method of the present invention, for removing a hazardous substance (20) in a gas atmosphere, using a hazardous substance removing material (10) in which a support (11) supports an antibody (12), humidity of an ambient atmosphere of the antibody (12) is controlled so that the antibody (12) becomes active.

Because water is essential to activate the antibody (12), an antigen-antibody reaction has been employed only for purifying aqueous solutions conventionally. By the above method, however, the antigen-antibody reaction can be applied to removal of the hazardous substance (20) in a gas phase atmosphere. Further, the antibody (12) captures a hazardous substance (20) specifically, and accordingly, appropriate selection of an antibody (12) attains highly precise removal in which a hazardous substance (20) to be captured is specified. In addition, some antibodies (12) themselves have a function of sterilizing and deactivating some kinds of hazardous substances (20). If the antibody (12) having a function of sterilizing and deactivating a target hazardous substance (20) is selected, it is unnecessary to incorporate the techniques for sterilizing and deactivating the hazardous substance (20).

In the hazardous substance removing method of the present invention, the support (11) may be made of a humidity control material that controls humidity of the ambient atmosphere of the antibody (12) so that the antibody (12) becomes active.

By the above method, the hazardous material (20) can be removed with the single use of the hazardous substance removing material (10).

A hazardous substance removing material (10) of the present invention, which is capable of being used in the hazardous substance removing method of the present invention, is composed of a support (11) that supports an antibody (12), wherein the support (11) is made of a humidity control material that controls humidity of an ambient atmosphere of the antibody (12) so that the antibody (12) becomes active.

With the above constitution, the antigen-antibody reaction can be applied to the removal of the hazardous substance (20) in the gas atmosphere and appropriate selection of an antibody (12) attains highly precise removal in which a hazardous substance (20) to be captured is specified. In addition, some antibodies (12) themselves have a function of sterilizing and deactivating some kinds of hazardous substances (20). If an antibody (12) having a function of sterilizing and deactivating a target hazardous substance (20) is selected, it is unnecessary to incorporate the techniques for sterilizing and deactivating the hazardous substance (20).

In the hazardous substance removing material (10) of the present invention, the antibody (12) is preferably chicken antibody (12).

The antibody (12) can be obtained by various methods. While, with the above constitution, the method for obtaining the antibody (12) from a chicken's egg attains easy mass production of the antibody (12), resulting in cost reduction of the hazardous substance removing material (10).

In the hazardous substance removing material (10) of the present invention, the support (11) is preferably subjected to antibacterial treatment and/or antifungal treatment.

The antibody (12) is principally a protein, and particularly, the chicken antibody (12) is food, and the antibody (12) may accompany a protein other than the antibody (12). These proteins might become the lure of multiplication of bacteria and mold (fungi). However, if the support (11) is subjected to antibacterial treatment and/or antifungal treatment as above, multiplication of the bacteria and the fungi is suppressed, so that the hazardous substance removing material (10) becomes suitable for long-term storage.

In the hazardous substance removing material (10) of the present invention, the antibody (12) may captures at least one hazardous substance (20) selected from bacteria, fungi, viruses, and allergens. Specifically, the bacteria include, for example, *Staphylococcus* (*Staphylococcus aureus, Staphylococcus epidermidis,* and the like), *Micrococcus, Bacillus anthracis, Bacillus cereus, Bacillus subtilis, Propionibacterium acnes,* and the like as Gram-positive bacteria, and *Pseudomonas aeruginosa, Serratia marcescens, Burkholderia cepacia, Streptococcus pneumoniae, Legionella pneumophilia, Mycobacterium tuberculosis,* and the like as Gram-negative bacteria. The fungi include, for example, *Aspergillus, Penicillius,* and *Cladosporium.* The viruses include influenza viruses, coronavirus (SARS virus), adenovirus, and rhinovirus. The allergens include pollens, mite allergens, and cat allergens. The hazardous substance removing material (10) of the present invention cannot deactivate the bacteria and the fungi out of the above substances, but exhibits a high adsorption effect to render them bacteriostatic while sterilizing and deactivating the viruses and the allergens.

In the hazardous substance removing material (10) of the present invention, the humidity control material forming the support (11) may be a fiber.

In this case, the fiber forming the support (11) may have an official moisture regain of 7% or higher in the hazardous substance removing material (10).

Water is essential to activate the antibody (12). With the above constitution, the fiber keeps much moisture, so that the humidity of the ambient atmosphere of the antibody (12) can be increased sufficiently for activating the antibody (12).

In the hazardous substance removing material (10) of the present invention, the antibody (12) may have an Fc (12b) that is bonded with the support (11).

With the above construction, the Fabs (12a) that capture the hazardous substance (20) are arranged outwards from the support (11) to increase contact probability of the hazardous substance (20) to the Fabs (12a), enabling efficient capturing of the hazardous substance (20).

In the hazardous substance removing material (10) of the present invention, the antibody (12) may be supported on the support (11) through a linker.

With the above construction, the degree of freedom of the antibody (12) on the support (11) becomes high to allow the antibody (12) to easily approach to the hazardous substance (20). Hence, removal performance is enhanced.

In the hazardous substance removing material (10) of the present invention, an indicator may be provided which detects an activity degree of the antibody (12) and outputs a signal when a detected activity degree becomes lower than a predetermined activity degree.

With the above constitution, whether the hazardous substance removing material (10) can be used and whether it should be replaced can be recognized.

In this case, the indicator may change in color when a detected activity degree becomes lower than the predetermined activity degree in the hazardous substance removing material (10).

With the above constitution, whether the hazardous substance removing material (10) can be used and whether it should be replaced can be judged at a glance.

In the hazardous material removing material (10) of the present invention, the antibody (12) lowers in its activity degree due to the existence of moisture.

Therefore, in the case of storing the hazardous substance removing material (10) of the present invention in a dry condition, in order to maintain the effect of the antibody (12), the hazardous substance removing material (10) is preferably stored hermetically in an atmosphere for storage at a temperature in a range between 18 and 25° C. and at a humidity of 40% or lower.

Alternatively, in the case of storing a hazardous substance removing material (10) in a wet condition, in order to maintain the effect of the antibody (12), it is preferable that a fiber is used as a humidity control material of the support (11) and water containing an activation stabilizer for the antibody (12) is penetrated in the fiber as the humidity control material. The activation stabilizer includes glycerol (glycerin), for example.

The hazardous substance removing material (10) of the present invention can be used directly as an air filter (10) and a wipe sheet (10).

Also, a mask (30) provided with the hazardous substance removing material (10) can be proposed.

In the case of the mask (30), it is preferable that the hazardous substance removing material (10) is interposed between a pair of air permeable outer and inner cloths (33, 34) and the air permeable inner cloth (33) has higher air permeability than the air permeable outer cloth (34).

With the above constitution, the air permeable inner cloth (33) has higher air permeability than the air permeable outer cloth (34), so that moisture included in human breath easily contacts with the hazardous substance removing material (10), accelerating activation of the antibody (12).

BEST MODE FOR CARRYING OUT THE INVENTION

An embodiment of the present invention will be described below in detail.

Figure 1:
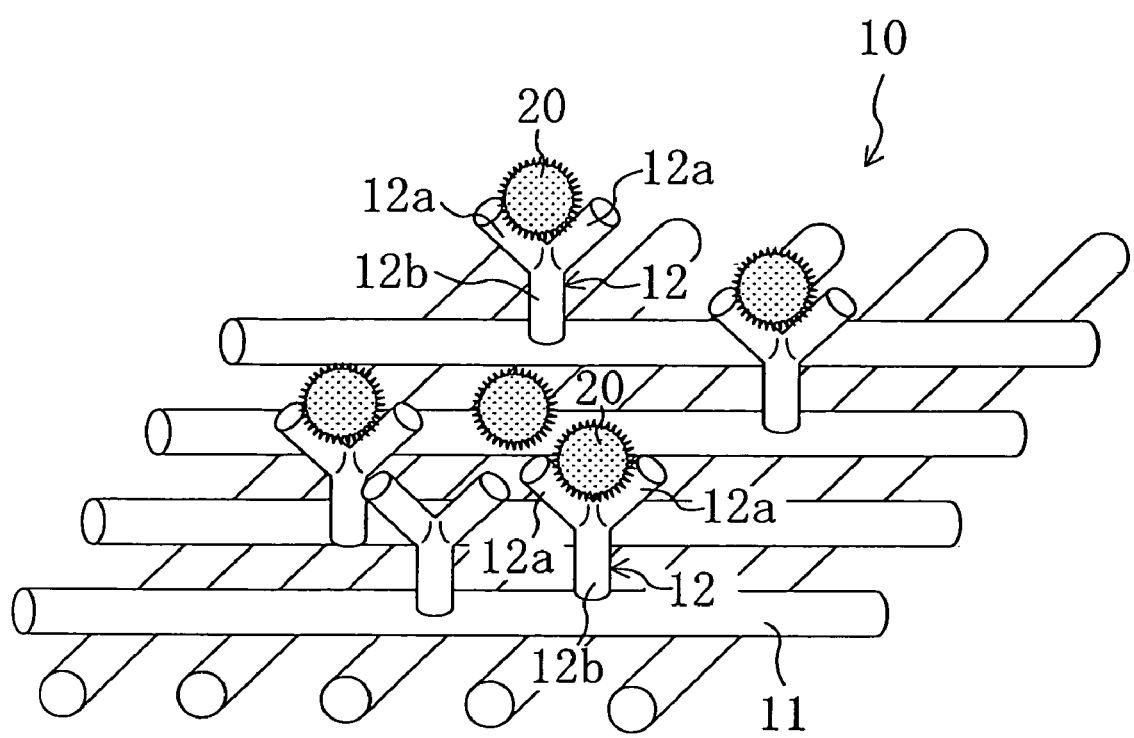
FIG. 1 is a view schematically showing an air filter (10) according to an embodiment of the present invention.

FIG. 1 shows a hazardous substance removing material (10) according to the embodiment of the present invention.

The hazardous substance removing material (10) is composed of a support (11) and an antibody (12) supported by the support (10).

The support (11) is made of a humidity control material that controls humidity of the ambient atmosphere of the antibody (12) so that the antibody (12) becomes active. Fibers may be used as the humidity control material, for example, and the support (11) may be composed of a woven fabric, a nonwoven fabric, or the like. In the case where a fiber composes the support (11), a large moisture content of the fiber is desired for adjusting the humidity of the ambient atmosphere of the antibody (12) so that the antibody (12) becomes active. Accordingly, the support (11) is preferably made of a fiber having an official moisture regain of 7.0% or higher, more preferably having an official moisture regain of 9.0% or higher, and the most preferably having an official moisture regain of 20% or higher. Wherein, the official moisture regain means a moisture percentage of a water-containing fiber which has been left for a long period of time in an atmosphere at 20° C. and at 65% RH (RH is relative humidity). Specifically, the official moisture regains of polyester and nylon as synthetic fibers, cotton, silk, and wool as a natural fibers, and rayon as a regenerated fiber are 0.3%, 3.5%, 7.0%, 9.0%, 16.0%, and 12.0%, respectively. In general, natural fibers and regenerated fibers have high official moisture regains while synthetic fibers have low official moisture regains. Wherein, synthetic fibers having special structures have 20% or higher official moisture regains The antibody (12) is a protein reactive (antigen-antibody reaction) specifically to a specified hazardous substance (antigen) (20), has a molecule size of 7 to 8 nm, and is in a Y-shaped molecular form. A pair of branch portions and a stem portion of the antibody (12) in the Y-shaped molecular form are called Fabs (12a) and Fc (12b), and the Fabs (12b) capture the hazardous substance (20).

A kind of the antibody (12) is determined so as to correspond to the kind of the hazardous substance (20) to be captured. The hazardous substance (20) to be captured by the antibody (12) includes bacteria, fungi, viruses, allergens, and Mycoplasmas. Specifically, the bacteria include, for example, *Staphylococcus* (*Staphylococcus aureus, Staphylococcus epidermidis*, and the like), *Micrococcus, Bacillus anthracis, Bacillus cereus, Bacillus subtilis, Propionibacterium acnes*, and the like as Gram-positive bacteria, and *Pseudomonas aeruginosa, Serratia marcescens, Burkholderia cepacia, Streptococcus pneumoniae, Legionella pneumophilia, Mycobacterium tuberculosis*, and the like as Gram-negative bacteria. The fungi include, for example, yeasts, *Aspergillus, Penicillius*, and *Cladosporium*. The viruses include influenza viruses, coronavirus (SARS virus), adenovirus, and rhinovirus. The allergens include pollens, mite allergens (mite decomposing products) and cat allergens (pet's dandruff). The antibody (12) cannot deactivate the bacteria and the fungi out of the above substances, but exhibits a high adsorption effect to render them bacteriostatic while sterilizing and deactivating the viruses and the allergens.

Referring to methods for producing the antibody (12), there are methods of: a method in which an antigen is administered to an animal such as a goat, a horse, a sheep, a rabbit, and the like and a polyclonal antibody (12) is refined from the blood thereof; a method in which spleen cells of an animal to which an antigen is administered and cultured cancer cells are subjected to cell fusion and a monoclonal antibody (12) is refined from a culture medium thereof or from a humor (ascites) of an animal in which the fussed cells are implanted; a method in which an antibody (12) is refined from a culture medium of genetically modified bacteria, plant cells, or animal cells to which antibody producing gene is introduced; and a method in which a chicken to which an antigen is administered is allowed to lay an immune egg and a chicken antibody (12) is refined from yolk powder obtained by sterilizing and splay-drying the yolk of the immune egg. Of all the above methods, the method for obtaining the antibody (12) from a chicken antibody enables easy mass production of the antibody (12), reducing the cost of the hazardous substance removing material (10).

It is preferable that the support (11) is subjected to antibacterial treatment such as coating of an agent containing an antibacterial agent and/or antifungal treatment such as coating of an agent containing an antifungal agent. The antibody (12) is principally a protein, and particularly, the chicken antibody (12) is food, and the antibody (12) may accompany a protein other than the antibody (12). These proteins might become the lure of multiplication of bacteria and fungi. However, if the support (11) is subjected to antibacterial and/or antifungal treatment, multiplication of the bacteria and the fungi is suppressed, so that the hazardous substance removing material (10) becomes suitable for long-term storage. The antibacterial/antifungal agents include organic silicon quaternary ammonium salts, organic quaternary ammonium salts, biguanides, polyphenols, chitosan, silver-support colloidal silica, zeolite-support silvers, and the like. As the treatments using them, there are a post-treatment in which an antibacterial/antifungal agent is immersed in or applied to the support (11) made of a fiber, a raw thread/raw cotton improving method in which an antibacterial/antifungal agent is mulled in the step of synthesizing a fiber composing the support (11), and the like.

Referring to methods for fixing the antibody (12) to the support (11), there are methods of: a method in which after a support (11) is subjected to silane treatment by γ-aminopropyl-triethoxysilane or the like, an aldehyde group is introduced on the surface of the support (11) by glutaraldehyde or the like to allow the aldehyde group and an antibody (12) to be in covalent bond; a method in which an untreated support (11) is immersed into an aqueous solution of an antibody (12) to cause ion boding, thereby fixing the antibody (12) to the support (11); a method in which an aldehyde group is introduced to a support (11) having a specified functional group to cause covalent bond between the aldehyde group and an antibody (12); a method in which a support (11) having a specified functional group is ion-bonded to an antibody (12); and a method in which a polymer having a specified functional group is coated on a support (11) and an aldehyde group is introduced to cause covalent bond between the aldehyde group and an antibody (12). Herein, the specified functional group includes the NHR group (R is an alkyl group of any of methyl, ethyl, propyl, and butyl except H), the $NH_2$ group, the $C_6H_5NH_2$ group, the CHO group, the COOH group, and the OH group.

Further, there is a method in which a functional group on the surface of a support (11) is changed into another functional group using BMPA (N-β-Meleimidopropionic acid) or the like to cause covalent bond between the thus changed functional group and an antibody (12) (the SH group is changed into the COOH group by BMPA).

Moreover, another method may be employed in which a molecule (Fc receptor, protein A/G, and the like) which is selectively bonded to the Fc (12b) of an antibody (12) is introduced on the surface of a support (11) to cause it to be bonded to the Fc (12b) of the antibody (12). In this case, the Fabs (12a) for capturing a hazardous substance (20) are arranged outwards from the support (11) to cause increase in contact possibility of the hazardous substance (20) to the Fabs (12a), resulting in efficient capturing of the hazardous substance (20).

The antibody (12) may be supported on the support (11) through a linker. In so doing, the degree of freedom of the antibody (12) on the support (11) increases, so that the antibody (12) is easy to reach the hazardous substance (20), attaining high removal performance. Bivalent or multivalent crosslinking reagent may be used as the linker. Specifically, there are listed maleimide, NHS (N-Hydroxysuccinimidyl) ester, imide ester, EDC (1-Ethyl-3-[3-dimetylaminopropyl] carbodiimido), PMPI (N-[p-Maleimidophenyl]isocyanete), which are selectively or non-selectively bonded to a target functional group (the SH group, the $NH_2$ group, the COOH group, and the OH group). Further, crosslinking agents have different crosslinking distances (spacer arm), and therefore, the distance can be selected within the range between about 0.1 nm and about 3.5 nm according to the target antibody (12). In view of efficient capturing of the hazardous substance (20), it is preferable to select a linker that will be bonded to the Fc (12b) of the antibody (12).

Referring to linker introduction, either of a method in which an antibody (12) bonded with a linker is further bonded to a support (11b) and a method in which an antibody (12) is bonded with a linker bonded to a support (11) are available.

The support (11) may support an indicator for detecting the activity degree of the antibody (12) and outputting a signal when the detected rate becomes lower than a predetermined activity degree. If such an indicator is supported, whether the hazardous substance removing material (10) can be used and should be replaced can be recognized. Especially, if a color of the indicator changes when the detected rate of the antibody (12) becomes lower than the predetermined activity degree, such judgments can be done at a glance. As the indicator, a polydiacetylene film can be employed which causes color change by operation such as pH change, temperature increase, dynamic stress, and the like.

Applied examples of the hazardous substance removing material (10) will be described below.

APPLIED EXAMPLE 1

The aforementioned hazardous substance removing material (10) may be used as an air filter (10) for an air conditioner and an air purification system.

With the air filter (10), the support (11) controls the humidity of the ambient atmosphere of the antibody (12) so that the antibody (12) becomes active, enabling application of the antigen-antibody reaction to air purification and contemplation of air purification with the single use of the air filter (10).

Further, the antibody (12) captures a hazardous substance (20) specifically, and therefore, highly precise air purification in which a hazardous substance (20) to be captured is specified can be performed by appropriate selection of the antibody (12).

Further, some kinds of antibodies (12) have a function of sterilizing and deactivating some kinds of hazardous substances (20), and therefore, it is unnecessary to combine the techniques for sterilizing and deactivating a target hazardous substance (20) if the antibody (12) has such the function to the target hazardous substance (20).

It is noted that the present invention may be applied to, rather than to the air filter (10) using the support (11) as the humidity control material, a combination of an air filter in which the support (11) made of a material other than a humidity control material supports the antibody (12) with a humidifier or a humidifying function of an air conditioner, whereby the humidity of the ambient atmosphere of the antibody (12) is controlled so that the antibody (12) becomes active.

APPLIED EXAMPLE 2

The aforementioned hazardous substance removing material (10) can be used as a mask (30).

Figure 2:
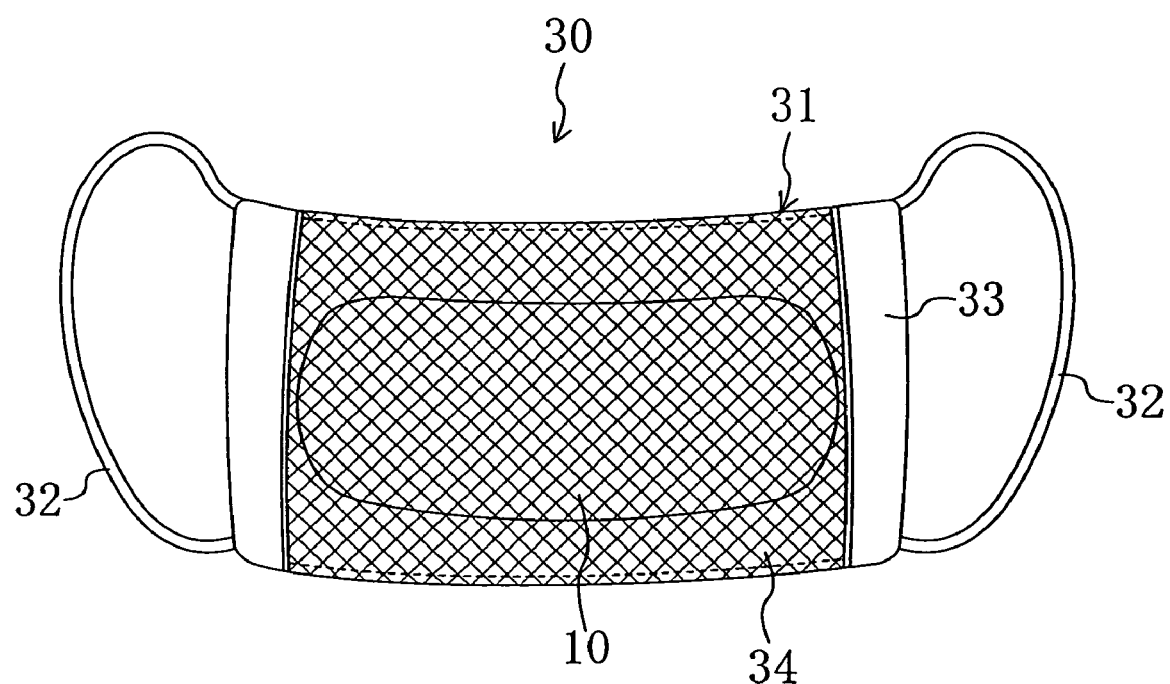
FIG. 2 is a view schematically showing a mask (30) according to the embodiment of the present invention.
Figure 3:
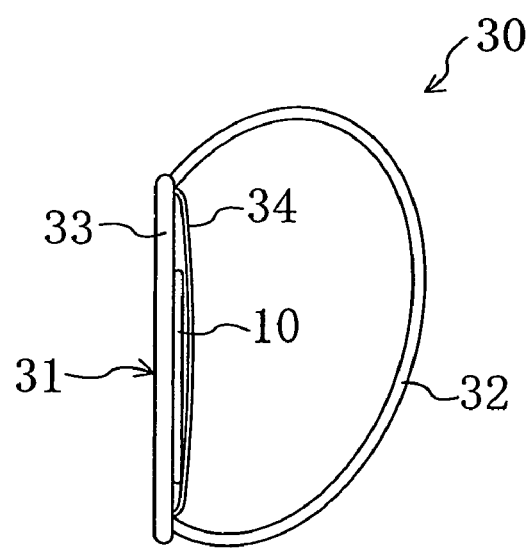
FIG. 3 is a side view of the mask (30) according to the embodiment of the present invention.

FIG. 2 and FIG. 3 show the mask (30) according to the embodiment of the present invention.

The mask (30) includes a rectangular mask body (31) and ear stopper strings (32) that connect paired ends of the minor sides of the mask body (31).

The mask body (31) is composed of an air permeable outer cloth (33) in which gauze woven fabrics are piled, a net-like air permeable inner cloth (34) forming a pocket inside the air permeable outer cloth (33), and the hazardous substance removing material (10) arranged inside the pocket.

In the mask (30), when the ability of the antibody (12) to remove the hazardous substance (20) becomes low, it can be increased only by replacing the hazardous substance removing material (10). The activation of the antibody (12) lowers in the existence of moisture, and therefore, the hazardous substance removing material (10) for replacement must be stored in a dry condition. For long-term maintenance of the effect of the antibody (12), it is preferable to hermetically store the hazardous substance removing material (10) in an atmosphere for storage at a temperature in the range between 18 and 25° C. and at a humidity of 40% or lower. Further, for suppressing bacteria multiplication, it is preferable to use an oxygen absorbent in combination or to perform purging by an inert gas or a nitrogen gas.

With the use of the mask (30), the antigen-antibody reaction can be applied to air purification in a gas atmosphere and highly precise, peculiar air purification in which a hazardous substance (20) to be captured is specified can be performed by appropriate selection of the antibody (12). Some kinds of antibodies (12) have a function of sterilizing and deactivating some kinds of hazardous substances (20), and therefore, it is unnecessary to combine the techniques for sterilizing and deactivating a target hazardous substance (20) if the antibody (12) has such the function to the target hazardous substance (20).

Moreover, the hazardous substance removing material (10) is interposed between the air permeable outer and inner cloths (33, 34) and the air permeable inner cloth (33) has higher air permeability than the air permeable outer cloth (34), resulting in easy contact of moisture contained in human breath to the hazardous substance removing material (10) to lead to acceleration of activation of the antibody (12).

It is noted that the hazardous substance removing material (10) is replaceable in the mask (30) in the above example, but the mask body itself may be composed of the hazardous substance removing material (10) replaceable as needed.

APPLIED EXAMPLE 3

The aforementioned hazardous substance removing material (10) may be used as a wipe sheet (10) in which the support (11) is in a sheet form.

The wipe sheet (10) may be stored in a dry condition as well as in the case of the replaceable hazardous substance removing material (10) of the aforementioned mask (30), or may be stored in a wet condition. The activation of the antibody (12) lowers in the existence of moisture. Therefore, for long-term maintenance of the effect of the antibody (12), the wipe sheet (10) to be stored in a wet condition is preferably stored in conditions that the humidity control material as the support (11) is made of a fiber and water containing an activation stabilizer for the antibody (12), such as glycerol, is penetrated in the fiber as the humidity control material.

With the wipe sheet (10), the antigen-antibody reaction can be applied to removal of the hazardous substance (20) in a gas atmosphere.

Further, highly precise, peculiar air purification in which a hazardous substance (20) to be captured is specified can be performed by appropriate selection of the antibody (12).

Moreover, some kinds of antibodies (12) have a function of sterilizing and deactivating some kinds of hazardous substances (20), and therefore, it is unnecessary to combine the techniques for sterilizing and deactivating a target hazardous substance (20) if the antibody (12) has such the function to the target hazardous substance (20).

INDUSTRIAL APPLICABILITY

The present invention is useful for a hazardous substance removing method such as air purification, a hazardous substance removing material (10) used therein such as an air filter (10), a mask (30), a wipe sheet (10), and the like, and a storage method thereof.

The invention claimed is:

1. A hazardous substance removing material in which a support supports an antibody, wherein
   the support is made of a humidity control material that controls humidity of an ambient atmosphere of the antibody so that the antibody becomes active,
   the humidity control material forming the support is a fiber and
   the fiber forming the support has an official moisture regain of 7% or higher.

2. A hazardous substance removing material in which a support supports an antibody, wherein
   the support is made of a humidity control material that controls humidity of an ambient atmosphere of the antibody so that the antibody becomes active, and
   an indicator is provided which detects an activity degree of the antibody and outputs a signal when a detected activity degree becomes lower than a predetermined activity degree.

3. The hazardous substance removing material of claim 2, wherein
   the indicator changes in color when a detected activity degree becomes lower than the predetermined activity degree.

4. An air filter in which a support supports an antibody, wherein
   the support is made of a humidity control material that controls humidity of an ambient atmosphere of the antibody so that the antibody becomes active,
   the humidity control material forming the support is a fiber and
   the fiber forming the support has an official moisture regain of 7% or higher.

* * * * *